(12) United States Patent
Fauritte et al.

(10) Patent No.: US 10,393,110 B2
(45) Date of Patent: Aug. 27, 2019

(54) PUMP CONNECTING THE INSIDE AND THE OUTSIDE OF A PRODUCT VESSEL

(71) Applicant: Nemera La Verpillière S.A.S., La Verpilliere (FR)

(72) Inventors: Francois Fauritte, Saint Priest (FR); Alain Regard, Beynost (FR)

(73) Assignee: Nemera La Verpillière (FR)

( * ) Notice: Subject to any disclaimer, the term of this patent is extended or adjusted under 35 U.S.C. 154(b) by 0 days.

(21) Appl. No.: 15/575,143

(22) PCT Filed: May 26, 2016

(86) PCT No.: PCT/FR2016/051236
§ 371 (c)(1),
(2) Date: Nov. 17, 2017

(87) PCT Pub. No.: WO2016/193575
PCT Pub. Date: Dec. 8, 2016

(65) Prior Publication Data
US 2018/0142683 A1    May 24, 2018

(30) Foreign Application Priority Data
May 29, 2015    (FR) .................................... 15 54901

(51) Int. Cl.
| F04B 53/10 | (2006.01) |
| B05B 11/00 | (2006.01) |
| A61M 35/00 | (2006.01) |
| F04B 9/06 | (2006.01) |
| F16K 15/04 | (2006.01) |

(52) U.S. Cl.
CPC ....... *F04B 53/1002* (2013.01); *A61M 35/003* (2013.01); *B05B 11/0041* (2018.08); *B05B 11/3067* (2013.01); *F04B 9/06* (2013.01); *F16K 15/04* (2013.01); *B05B 11/0059* (2013.01); *B05B 11/3074* (2013.01)

(58) Field of Classification Search
CPC . A61M 35/003; B05B 11/004; F04B 53/1002
USPC ........................ 222/321.7, 321.9, 383.1, 628
See application file for complete search history.

(56) References Cited

U.S. PATENT DOCUMENTS 4,371,098 A * 2/1983 Nozawa ............. B05B 11/0059
                                                    137/853
4,817,829 A * 4/1989 Fuchs ................. B05B 11/0051
                                                    141/27

(Continued)

FOREIGN PATENT DOCUMENTS

EP    1295811 A1    3/2003
EP    1578537 B1    9/2005

*Primary Examiner* — Vishal Pancholi
(74) *Attorney, Agent, or Firm* — St. Onge Steward Johnston & Reens, LLC

(57) ABSTRACT

A pump for connecting the inside and the outside of a product vessel for pharmaceutical use including an upstream end for passing a product intended for extending into the vessel and for being in fluid communication with the vessel and, downstream from the upstream end, a check valve switching between configurations for sealing and passing a product. The upstream end is extended upstream by a member forming a passage of a product in a labyrinth, referred to as labyrinth-forming member.

10 Claims, 2 Drawing Sheets

(56) References Cited

U.S. PATENT DOCUMENTS

| | | | | |
|---|---|---|---|---|
| 5,397,059 | A * | 3/1995 | Baudin | B05B 7/066 |
| | | | | 222/321.2 |
| 5,813,571 | A * | 9/1998 | Gaucher | B05B 11/0043 |
| | | | | 222/105 |
| 5,979,712 | A * | 11/1999 | Montaner | B05B 11/0059 |
| | | | | 222/321.4 |
| 6,257,455 | B1 * | 7/2001 | Trepina | B05B 11/0016 |
| | | | | 222/189.09 |
| 6,302,304 | B1 * | 10/2001 | Spencer | B05B 11/3001 |
| | | | | 222/260 |
| 6,779,690 | B2 * | 8/2004 | Masuzzo | B05B 11/0059 |
| | | | | 222/222 |
| 2003/0121940 | A1 * | 7/2003 | Ichikawa | B05B 11/3001 |
| | | | | 222/321.6 |
| 2006/0005389 | A1 * | 1/2006 | Bougamont | B05B 11/3067 |
| | | | | 29/890.124 |
| 2008/0179272 | A1 * | 7/2008 | Gardet | B05B 11/3047 |
| | | | | 215/40 |

* cited by examiner

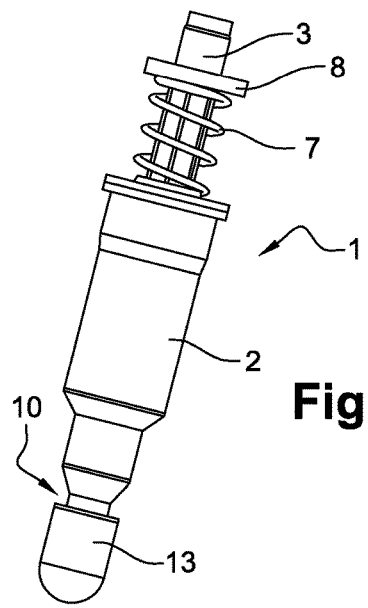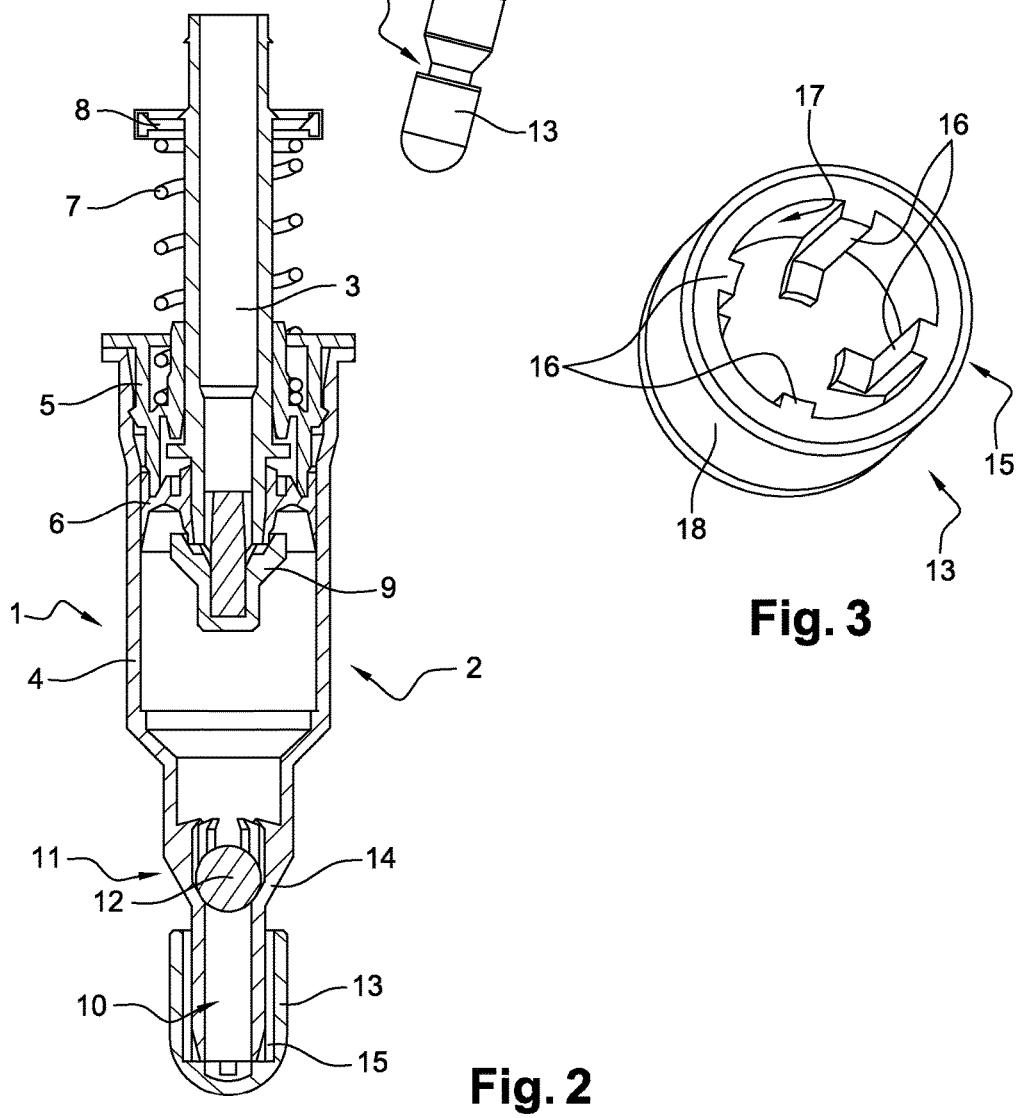

PUMP CONNECTING THE INSIDE AND THE OUTSIDE OF A PRODUCT VESSEL

FIELD OF THE INVENTION

The invention relates to the field of pharmaceutical product dispensing devices.

BACKGROUND OF THE INVENTION

It relates more particularly to pumps intended to connect the inside and the outside of a pharmaceutical product vessel, the product being for example a liquid or gel of low viscosity used in the treatment of adult men having a testosterone deficiency.

It is important, in the treatment of certain complaints, to ensure that the quantity of pharmaceutical product dispensed by a device with a pump for dispensing this product, or dose to be dispensed, is always substantially identical.

In the following, an element is qualified as upstream or downstream as a function of the direction of the flow of the product during dispensing thereof in this element.

Document EP 1 578 537 discloses a pharmaceutical product dispensing device provided with a pump intended to connect the inside and the outside of a pharmaceutical product vessel. It comprises an upstream product passage end intended to extend into the vessel and a ball-type nonreturn valve extending downstream of the upstream end, the valve switching between closure and passage configurations. This device is intended to be used "head up".

This device makes it possible to efficiently dispense the same dose of product as long as the vessel is sufficiently full, but when the quantity of product remaining in the vessel corresponds to no more than a few doses (this is referred to as the end of life of the device), it is perceived that these are not as regular as the doses dispensed beforehand.

Specifically, during the initial mounting of the device, air is retained in the pump.

Subsequently, the devices are packaged in cardboard boxes which may be stored in random orientations.

Consequently, the device may be stored, before its first use by the patient, in a position in which the vessel is above the upstream end (when the device is "head down" with respect to its position allowing the product to be dispensed), which means that the ball of the nonreturn valve is moved downward under the effect of gravity and no longer completely closes the passage of the upstream end. The effect of this is that the air contained in the pump manages progressively to pass, from the upstream end, into the vessel. Although a majority of this air is expelled during the first use of the device, another portion can be trapped at the bottom of the vessel, and thus have an influence on the content of the last doses to be dispensed.

SUMMARY OF THE INVENTION

The object of the invention is to provide a pump intended to connect the inside and the outside of a product vessel that makes it possible to ensure that the doses dispensed by the device will be more regular until the end of life of the device, whatever the quantity of product in the vessel and the storage conditions of the device.

To this end, the subject of the invention is a pump intended to connect the inside and the outside of a pharmaceutical product vessel, comprising an upstream product passage end intended to extend into the vessel and to be in fluid communication with the vessel and, downstream of the upstream end, a nonreturn valve switching between closure and passage configurations, characterized in that the upstream end is extended upstream by a member forming a labyrinth-type product passage, termed labyrinth-forming member.

The term "labyrinth-type product passage" means a passage in which the product that is situated therein must follow a twisting path to emerge therefrom. Such a passage is configured to create a "labyrinth" effect, which an effect of resistance to the flow of a fluid.

It is observed that, by virtue of the presence of the labyrinth-forming member extending the upstream end of the pump, the passage of the air retained initially in the pump from this pump toward the vessel is limited, or even prevented, by the labyrinth effect.

Thus, the air present initially in the pump during the mounting of the product dispensing device comprising the pump will have no influence, or at least a limited influence, on the quantity of product to be dispensed. The doses dispensed by the device will therefore be identical whether the vessel is full or virtually empty of product.

In one particular embodiment of the invention, the upstream end is of tubular general shape.

In one particular embodiment of the invention, the labyrinth-forming member has a general bell shape.

In one particular embodiment of the invention, the labyrinth-forming member is provided with means for centering with respect to the upstream end.

In one particular embodiment of the invention, the centering means cooperate with the inside of the upstream end.

In one particular embodiment of the invention, the centering means comprise centering stops distributed circumferentially inside of the upstream end.

In one particular embodiment of the invention, the centering means cooperate with the outside of the upstream end.

In one particular embodiment of the invention, the centering means comprise centering stops distributed circumferentially around the upstream end.

The invention also relates to an assembly of a pump and of a flexible pouch forming a pharmaceutical product vessel, characterized in that the pump is in accordance with the invention.

The invention also relates to a device for dispensing a product for pharmaceutical use comprising a pump, characterized in that this pump is in accordance with the invention.

BRIEF DESCRIPTION OF THE DRAWINGS

The invention will be better understood on reading the following description of the appended figures which are provided by way of examples and have no limiting nature, in which:

FIG. 1 is a perspective view of a pump of a pharmaceutical product dispensing device according to a first embodiment of the invention;

FIG. 2 is a view in axial section of the pump of FIG. 1;

FIG. 3 is a perspective view of the labyrinth-forming member of the pump of FIG. 1;

DETAILED DESCRIPTION OF THE INVENTION

FIG. 1 shows a device 1 for dispensing a pharmaceutical product in the form of liquid or gel of low viscosity. This is, for example, a liquid used in the treatment of adult men having a testosterone deficiency.

Figure 4:
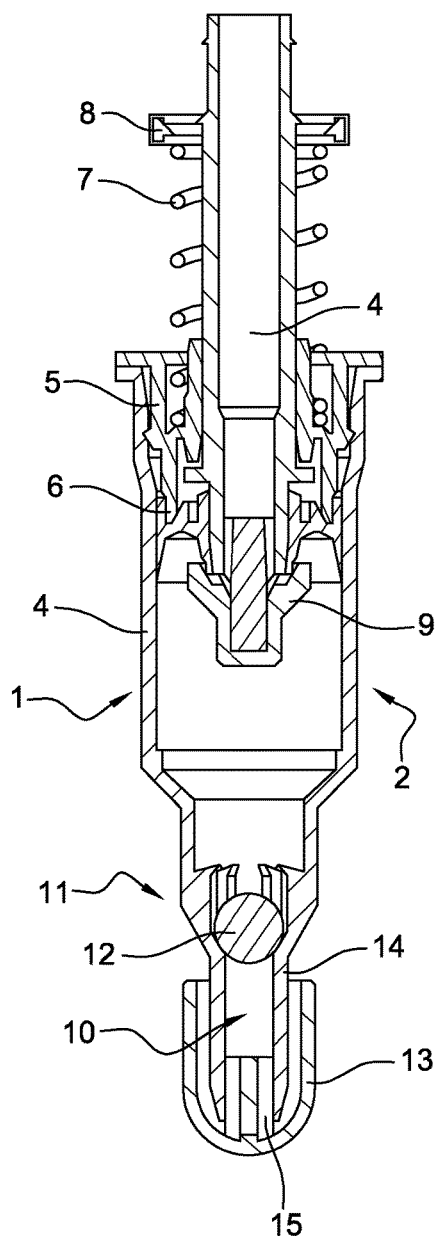
FIG. 4 is a view similar to that of FIG. 2 showing a pump according to a second embodiment of the invention.

As can be seen in FIGS. 2 and 4, the dispensing device 1 comprises a pump 2 actuated by a nozzle 3 and intended to connect the inside and the outside of a vessel (not shown), which is for example a flexible pouch containing the liquid or gel of low viscosity. The pump 2 is provided with a body 4, a guide ring 5 and a piston 6 loaded by a spring 7 bearing between the guide ring 5 and an upper stop 8 borne by the nozzle 3. The pump 2 also comprises a lower stop 9 which, in a rest position of the nozzle 3, isolates the inside of the body 4 from the outside.

In the following, an element is qualified as upstream or downstream as a function of the direction of the flow of the product during dispensing thereof in this element.

The pump 2 comprises an upstream product passage end 10 intended to extend into the vessel and to be in fluid communication therewith. The upstream end 10 is of tubular general shape.

FIGS. 2 and 4 show the dispensing device 1 in the use position, or "head up" position, that is to say in a position in which the vessel is intended to be below the upstream end 10. Thus, in FIGS. 2 and 4, the upstream direction is directed toward the bottom of the figures and the downstream direction toward the top of the figures.

The pump 2 comprises, downstream of the upstream end 10, a nonreturn valve 11, for example a nonreturn valve with a ball 12.

The nonreturn valve 11 is able to switch between a configuration for closing the upstream end 10 and a configuration allowing passage therethrough. In FIGS. 2 and 4, the nonreturn valve 11 is represented in its closure configuration, corresponding to the position in which the ball 12 closes the passage of the upstream end 10.

The upstream end 10 is extended upstream, that is to say toward the bottom of FIGS. 2 and 4, by a member 13 forming a labyrinth-type product passage, termed labyrinth-forming member.

In the examples illustrated, the labyrinth-forming member 13 has a general bell shape.

The labyrinth-forming member 13 can cover a variable length of the upstream end 10, and is not limited to that of the examples illustrated.

Owing to the presence of the labyrinth-forming member 13 extending the upstream end 10, the air contained in the pump 2, which could possibly pass between the ball 12 and the wall 14 of the upstream end 10 serving as a seat for the ball 12, must follow the labyrinth passage formed by the bell shape of the labyrinth-forming member 13 before reaching the vessel.

Thus, when the dispensing device 1 is placed "head down" and the ball 12 of the nonreturn valve 11 is moved downward under the effect of gravity, the air contained in the pump 2 which could possibly be introduced into the passage of the upstream end 10 does not reach the vessel, or only reaches it in a limited manner.

In the two embodiments presented in the figures, the labyrinth-forming member 13 is provided with means 15 for centering with respect to the upstream end 10.

In a first embodiment of the invention presented in FIGS. 2 and 3, the centering means 15 cooperate with the outside of the upstream end 10 (see in particular FIG. 2).

To this end, as can be seen in FIG. 3 representing the labyrinth-forming member 13 alone, the centering means 15 comprise centering stops 16 intended to be distributed circumferentially around the upstream end 10.

For example, the centering stops 16 are integrally formed with the internal face 17 of an annular wall 18 of the labyrinth-forming member 13.

In the particular embodiment represented in FIG. 3, the centering stops 16 are four in number and are distributed uniformly on the internal face 17 of the annular wall 18 of the labyrinth-forming member 13.

In variants not represented, the centering stops 16 number two, three or five, for example, and are distributed uniformly on the internal face 17 of the annular wall 18. It will be noted, however, that the centering stops 16 are not necessarily distributed uniformly on the internal face 17 of the annular wall 18.

Figure 5:
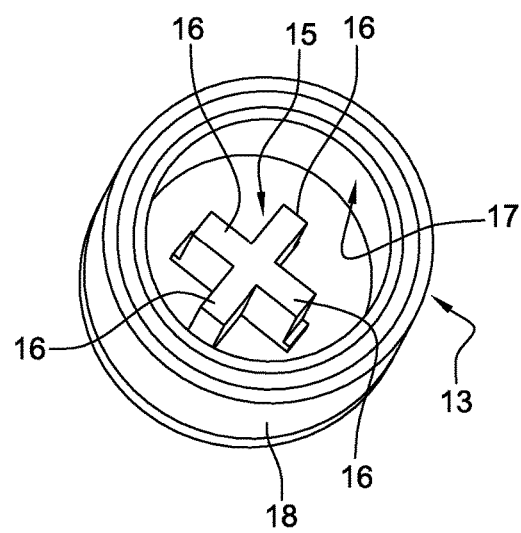
FIG. 5 is a view similar to that of FIG. 3 showing the labyrinth-forming member of the pump of FIG. 4.

In a second embodiment of the invention presented in FIGS. 4 and 5, the centering means 15 cooperate with the inside of the upstream end 10 (see in particular FIG. 4).

To this end, as can be seen in FIG. 5 representing the labyrinth-forming member 13 alone, the centering means 15 comprise centering stops 16 intended to be distributed circumferentially inside the upstream end 10.

In the particular embodiment represented in FIG. 5, the centering stops 16 form a star with four branches that is centered on the axis of the labyrinth-forming member 13.

In other variants not represented, the centering stops 16 form a star comprising a different number of branches, for example three, five or six.

It will be noted, however, that the centering stops are not necessarily distributed uniformly about the axis of symmetry of the labyrinth-forming member nor centered on the axis of the labyrinth-forming member.

In a general manner, the invention is not limited to the embodiments presented and other embodiments will become clearly apparent to a person skilled in the art.

The invention claimed is:

1. A pump to connect an inside and an outside of a pharmaceutical product vessel, comprising:
    an upstream product passage end extending into the vessel and being in fluid communication with the vessel such that fluid product flows into the pump via the upstream product passage end,
    a nonreturn valve, downstream of the upstream end, switching between closure and product passage configurations, and
    wherein the upstream end is extended upstream by a labyrinth-forming member forming a labyrinth-type product passage through which the fluid product can flow having an entrance and an exit, wherein the fluid product follows a path that successively changes direction at least twice between the entrance and the exit of the labyrinth-type passage.

2. The pump according to claim 1, in which the upstream end is of tubular general shape.

3. The pump according to claim 1, in which the labyrinth-forming member has a general bell shape.

4. The pump according to claim 1, in which the labyrinth-forming member is provided with centering stops centering the upstream end.

5. The pump according to claim 4, in which the centering stops cooperate with the inside of the upstream end.

6. The pump according to claim 5, in which the centering stops are distributed circumferentially on the inside of the upstream end.

7. The pump according to claim 4, in which the centering stops cooperate with the outside of the upstream end.

8. The pump according to claim 7, in which the centering stops are distributed circumferentially around the upstream end.

9. An assembly of a pump and of a flexible pouch forming a pharmaceutical product vessel, comprising a pump according to claim 1.

10. A pharmaceutical product dispensing device comprising a pump according to claim 1.

\* \* \* \* \*